United States Patent
Winston et al.

(10) Patent No.: US 7,135,163 B2
(45) Date of Patent: Nov. 14, 2006

(54) PREVENTION OF CRYSTAL FORMATION IN TOOTHPASTE

(75) Inventors: Anthony Winston, East Brunswick, NJ (US); Bruce Conley, Hamilton Square, NJ (US); Bruce J. Nelson, Dayton, NJ (US); Carl Mayer, Woodbury Heights, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 350 days.

(21) Appl. No.: 10/686,879

(22) Filed: Oct. 16, 2003

(65) Prior Publication Data

US 2005/0084460 A1  Apr. 21, 2005

(51) Int. Cl.
*A61K 8/46* (2006.01)
*A61Q 11/00* (2006.01)

(52) U.S. Cl. .......................................... 424/52; 424/57
(58) Field of Classification Search .................. None
See application file for complete search history.

(56) References Cited

U.S. PATENT DOCUMENTS

| | | | |
|---|---|---|---|
| 4,515,772 A | 5/1985 | Parran et al. | 424/57 |
| 4,590,066 A | 5/1986 | Parran et al. | 424/52 |
| 4,684,518 A | 8/1987 | Parran et al. | 424/52 |
| 5,000,973 A * | 3/1991 | Scaglione et al. | 426/549 |
| 5,318,773 A | 6/1994 | Winston et al. | 424/52 |
| 5,599,526 A * | 2/1997 | Viscio et al. | 424/49 |
| 5,603,922 A | 2/1997 | Winston et al. | 424/49 |
| 5,605,675 A | 2/1997 | Usen et al. | 424/49 |
| 5,833,957 A | 11/1998 | Winston et al. | 424/49 |
| 5,858,333 A | 1/1999 | Winston et al. | 424/57 |
| 6,159,448 A | 12/2000 | Winston et al. | 424/52 |
| 2005/0147719 A1 * | 7/2005 | Hill et al. | 426/132 |

* cited by examiner

*Primary Examiner*—Frederick Krass
(74) *Attorney, Agent, or Firm*—Frenkel & Associates

(57) ABSTRACT

In dentifrices containing sodium bicarbonate and anionic species which can react with sodium and water to precipitate hydrated crystals, the ratio of water to humectants, abrasives, and/or thickeners is adjusted so that the dentifrice has a water activity of no greater than 0.60 so as to greatly reduce the salting out of the anionic species.

22 Claims, No Drawings

PREVENTION OF CRYSTAL FORMATION IN TOOTHPASTE

FIELD OF THE INVENTION

The present invention is directed to toothpastes which contain baking soda and to providing stable toothpaste formulations containing same.

BACKGROUND OF THE INVENTION

The use of bicarbonate salts (baking soda) as a dentifrice or the incorporation of such salts into dentifrice compositions is well known in the art of oral care. A renewed interest in incorporating bicarbonate salts into toothpaste has emerged in light of the success of the present assignee's Dental Care® and PeroxiCare® products. The addition of bicarbonate salts into dentifrices is beneficial for several reasons such as for providing good plaque removing capabilities, as well as for improving the whitening properties of dentifrices. Importantly, bicarbonate salts provide a clean fresh feeling in the oral cavity after brushing and rinsing with water.

In formulating toothpastes containing high levels of sodium bicarbonate, one of the difficulties can be the incorporate of certain anions, which are added to bestow on the formulation certain benefits. The concentration of sodium ions present in the liquid phase of the toothpaste can lead to salting out of these anions as crystal hydrates of their sodium salts. Often these hydrated sodium salts undesirably precipitate as large crystals.

Thus, for example, in formulating a sodium bicarbonate-containing tartar control toothpaste it is desirable to add a pyrophosphate salt. Tartar, known also as calculus, is a hard mineralized deposit which forms around teeth. This formation arises from deposition of crystals of calcium phosphate in the pellicle and the extra-cellular matrix of dental plaque. Various forms of calcium phosphate have been identified but the most difficult to remove and thermodynamically most stable form is called hydroxyapatite (HAP). Amorphous forms of calcium phosphate are believed to be the precursors of HAP. Regular brushing can usually remove the amorphous forms but is not fully effective to dislodge the final stable calculus form. Therefore it is desirable to prevent amorphous forms of calcium phosphate from transforming into HAP. The art has recognized that agents which interfere with the formation of HAP crystallization will be effective anti-tartar agents.

Soluble inorganic pyrophosphate salts have over the last decade set the commercial standard as tartar control agents. This technology has been reported by Parran, Jr. et al. in a series of patents including U.S. Pat. No. 4,590,066, U.S. Pat. No. 4,515,772 and U.S. Pat. No. 4,684,518.

However, in the presence of high concentrations of sodium ions provided by the sodium bicarbonate, disodium dihydrogen pyrophosphate hexahydrate or tetrasodium pyrophosphate decahydrate can precipitate as large crystals.

Similarly, in formulating a bicarbonate-based toothpaste containing a remineralization promoting system, orthophosphate is required. The primary component of the enamel and dentin in teeth is calcium phosphate in the form of calcium hydroxyapatite. This material is highly insoluble at normal oral pHs. However, carious lesions (demineralization) form in teeth when the teeth are subjected to acids produced from the glycolysis of sugars by the action of various oral bacteria. This is because calcium phosphate salts are more soluble in acidic media.

Saliva is supersaturated with respect to calcium and phosphate ions. Saliva therefore helps protect teeth against demineralization and can slowly remineralize teeth which have become demineralized by acids. It is well known that the presence of fluoride ions can enhance the natural remineralization process and this is one of the accepted mechanisms by which fluoride toothpastes and rinses protect against caries. The efficacy of fluoride-containing toothpastes and rinses to remineralize teeth is limited by the modest levels of calcium and phosphate in saliva. It is evident from the prior art that it is highly desirable to increase the available concentration of calcium and phosphate ions in the oral cavity to speed up the remineralization process. However, because of calcium phosphate's low solubility at the pH of saliva, the addition of higher levels of dissolved calcium and phosphate ions is not easily accomplished.

Oral products designed to remineralize subsurface lesions in teeth and mineralize exposed dentinal tubules, i.e., remineralizing/mineralizing products, are disclosed, for example, in U.S. Pat. No. 5,603,922; 5,605,675; 6,159,448; 5,833,957; and 5,858,333, all to Winston and Usen. It is believed that the first remineralizing dentifrice made available to the public was based on the Winston and Usen patents. These patents describe a two-part product comprising a first part comprising a calcium salt and a second part comprising phosphate and fluoride salts which are kept separate in a tube by a physical divider but wherein both parts are dispensed simultaneously from the tube on the tooth brush applicator. In a bicarbonate-based remineralizing toothpaste, the calcium component would be separated from the fluoride, phosphate and bicarbonate components as two phases. The calcium phase would contain a calcium salt and other conventional toothpaste ingredients while the other phase would contain phosphate, bicarbonate and fluoride sources in a base of water, humectants and other toothpaste ingredients. Unfortunately, problems arise because the addition of phosphate salts to the phase containing sodium bicarbonate and fluoride can result in the formation of large crystals of hydrated mono, di, or trisodium orthophosphate sometimes also containing fluoride ions.

SUMMARY OF THE INVENTION

Surprisingly, it has been found that by lowering the water activity of sodium bicarbonate-containing toothpastes below about 0.60, anions such as pyrophosphate and orthophosphate can be prevented from precipitating as large hydrated crystals. By water activity is meant the equilibrium vapor pressure of water above the toothpaste, when kept in a sealed container, divided by the saturated vapor pressure of the water measured at the same temperature.

The water activity of the toothpaste is a function of the ratio of water to humectant in the formulation, as well as to the content of thickeners, abrasives, and other dissolved species. By lowering the ratio of water to humectant, or by increasing the content of thickeners or other material which bind water, the water activity can be lowered.

DETAILED DESCRIPTION OF THE INVENTION

The dentifrices of the present invention include toothpastes, dental creams, or dental gels. They comprise the several essential, as well as optional, components disclosed hereinafter.

A dentifrice is a substance or preparation used with a toothbrush to aid mechanical cleaning of the accessible surfaces of the teeth. A typical formulation for a dentifrice (e.g., toothpaste) contains varying amounts of humectants, organic thickeners and gums, inorganic thickeners, and flavors and sweeteners. Most dentifrices contain one or more active components to reduce decay, reduce or remove tartar buildup, reduce sensitivity, or provide for remineralization, for example.

The most widely used active in dentifrices is a water-soluble fluoride ion source which is effective as an anticaries agent. Fluoride ion sources thus useful include inorganic fluoride salts, such as soluble alkali metal or alkaline earth metal salts, for example, sodium fluoride, potassium fluoride, sodium fluorosilicate, ammonium fluorosilicate, sodium fluorozirconate or sodium monofluorophosphate. Alkali metal fluorides such as sodium fluoride, or sodium monofluorophosphate, and mixtures thereof, are particularly useful.

The amount of the soluble fluoride ion source in the dentifrice is dependent on the particular compounds used and the type of dentifrice, but it must be incorporated in an effective but nontoxic amount, generally up to about 5.0% of the preparation. Any suitable minimum amount of such compound may be used, but it is preferable to employ a sufficient quantity as to release about 25 up to a maximum of 5,000 ppm, preferably about 850 to 1500 ppm. of fluoride ion. Typically, in the case of sodium fluoride the fluoride ion source is present in an amount from 0.05% to 0.65% by weight, based on the weight of the dentifrice. In the case of sodium monofluorophosphate the compound may be present in an amount of about 0.2–2% by weight.

In the dentifrices of this invention, sodium bicarbonate is incorporated as both an anticalculus adjuvant and an abrasive. Commonly assigned U.S. Pat. No. 5,318,773 illustrates the use of sodium bicarbonate as an anticalculus adjuvant. The entire content of this patent is herein incorporated by reference. As previously recognized, the bicarbonate salt provides a clean, fresh feeling in the mouth after brushing and rinsing with water, and as such, toothpastes containing bicarbonate have been very successful in the marketplace. Desirably, the sodium bicarbonate is provided in particulate from having a mean particle size within the range of about 5μ to 200μ, preferably about 20μ to 120μ, in diameter. The bicarbonate particles may be incorporated in the dentifrice in varying amounts, depending upon the particular formulation, e.g., toothpaste or gel, so long as it is present in an amount effective to impart the desired abrasive characteristics and, if desired, to promote inhibition of calculus formation when the dentifrice is applied to the teeth. Accordingly, as used herein, the term "effective" or "effective amount" means a sufficient amount of the ingredient being utilized to provide the desired effect or result. In a dentifrice such as a toothpaste or gel, the amount of sodium bicarbonate included to provide effective abrasive action and provide a fresh feel in the oral cavity is from about 7% to 65% by weight based on the weight of the formulation.

Unfortunately, in the presence of sodium ions provided by the sodium bicarbonate, anionic species provided, for example, as active agents in the dentifrice, can precipitate as large crystals, providing a gritty toothpaste and reducing the effectiveness of the salts which are added as actives. Thus, for example, anionic species with a tendency to form large crystals of hydrated sodium salts include orthophosphates, pyrophosphates, tripolyphosphates, metaphosphates, borates, thiosulfates, glycerolphosphates, etc. While precipitation of the hydrated sodium salts can be reduced by greatly reducing the water content of the dentifrice, water is often necessary to provide a uniform mixing of the components of the dentifrice, provide the proper viscosity for the dentifrice so it can flow from the tube or effectively coat the teeth if used as a professional gel and the like, and/or provide a toothpaste consistency that is pleasing when placed in the oral cavity during brushing. Accordingly, the dentifrices of the present invention should have a water content of at least 5 wt. % based on the total weight of the dentifrice formulation. Water contents of at least 7 wt. % are particularly useful.

The soluble pyrophosphate salts are examples of active agents which may be incorporated in the dentifrices of the present invention. Such salts are known for reducing and preventing tartar formation on the teeth and include mono-, di-, tri- or tetra-alkali metal pyrophosphates and mixtures thereof. Specific non-limiting examples of useful pyrophosphate salts include disodium pyrophosphate, tetrasodium pyrophosphate, tetrapotassium pyrophosphate, and mixtures thereof. The pyrophosphates may be employed in their anhydrous as well as their hydrated forms.

As disclosed in previously mentioned U.S. Pat. No. 5,318,773, dentifrices containing such sodium bicarbonate/alkali metal pyrophosphate mixtures together with a water-soluble fluoride ion source and other conventional dentifrice constituents, exhibit enhanced anticalculus properties. Such dentifrices may utilize decreased concentrations of total pyrophosphate salts and yet have significant anticalculus activity. Moreover, such dentifrices exhibit effective anticalculus activity notwithstanding the fact that they may contain substantially less than 1.5% dissolved pyrophosphate ion and amounts of undissolved tetrasodium pyrophosphate decahydrate in high proportions. In this invention, the water activity of sodium bicarbonate dentifrices is controlled so as to reduce the salting-out effect of the sodium bicarbonate ingredient on pyrophosphate salts that may be incorporated for anti-tartar control.

Another anionic additive which can be incorporated into a toothpaste is inorganic phosphate salts which, when added to a dentifrice and separated from an added water soluble or partially water soluble calcium salt, provide the dentifrice with an enhanced remineralization formula. In such formulas, the calcium and phosphate salts preferably under the influence of fluoride are taken up by the tooth surfaces and combine, eventually to form calcium hydroxyapatite and/or fluoroapatite to remineralize precarious lesions and the like. U.S. patents to Winston and Usen disclosing the separate calcium and phosphate salts have been described above and are herein incorporated by reference. Again, however, in the presence of sodium bicarbonate, the phosphate ion can salt out as a hydrated sodium salt. This salting out is increased in the presence of fluoride and mixed hydrated sodium phosphate fluoride is produced. If this occurs, large undesirable crystals are formed, which could be mistaken by uses for foreign material e.g. glass. Examples of water-soluble inorganic phosphates which can be used in remineralization formulas of the invention include, for example, and the di- or tri-alkali and ammonium salts of orthophosphoric acid, such as di- or tri-sodium, potassium, sodium, or ammodium orthophosphate. Dipotassium phosphate is particularly useful. The concentration of the phosphate ions in the remineralization dentifrice formulation typically is from about 250 to 40,000 ppm.

To prevent the salting out of the hydrated sodium salts of the above anionic components and others, it has been found that the water activity of the sodium bicarbonate-containing dentifrices must be lowered to below about 0.60. By water activity is meant the equilibrium vapor pressure of water above the dentifrice, such as when kept in a sealed container, divided by the saturated water pressure of water measured at the same temperature. Since the water activity of the hydrated crystals, which undesirably form, is about 0.30, it is somewhat surprising that crystal formation can be prevented in toothpastes with water activities approaching 0.60 representing conditions thermodynamically favorable to crystal formation. Accordingly, it was thought that the water content, or the water activity, needed to be no higher than about 0.30. The water activity of the toothpaste is a function of the ratio of water to humectant in the formulation, as well as to the content of thickeners, abrasives, and other dissolved species. By lowering the ratio of water to humectant, or by increasing the content of thickeners or other materials which bind water, the water activity can be lowered. Again, it is important that a sufficient water content be present in the dentifrice so as to provide a dentifrice with desired properties. As stated previously, the level of water should be at least about 5 wt. % of the dentifrice.

The toothpaste, gel or other liquid vehicle may also contain, if desired, a conventional abrasive or polishing material, in addition to the sodium bicarbonate. Conventional water-insoluble abrasives which are so useful include sodium metaphosphate, potassium metaphosphate, tricalcium phosphate, calcium phosphate dehydrate, anhydrous dicalcium phosphate, calcium pyrophosphate, magnesium orthophosphate, trimagnesium phosphate, calcium carbonate, aluminum silicate, zirconium silicate, hydrated silica, hydrated alumina, bentonite, and mixtures thereof.

Preferred abrasive materials which may be admixed with the sodium bicarbonate include hydrated silica, silica gel or colloidal silica, and complex amorphous alkali metal aluminosilicates. When visually clear gels are employed, polishing agents of hydrated or colloidal silica, alkali metal aluminosilicate complexes and alumina are particularly useful, since they have refractive indices close to the refractive indices of gelling agent-liquid (including water and/or humectant) systems commonly used in such dentifrices.

Any of the foregoing water-insoluble abrasives may be present as an adjunct or secondary abrasive in concentrations of up to about 50%, preferably, in amounts up to about 20%, by weight of the dentifrice.

Organic surface-active agents can be used in the dentifrices of the present invention to achieve increased cleaning action, assist in achieving thorough and complete dispersion of the anticalculus agent throughout the oral cavity, and improve the detergent and foaming properties of the dentifrices. Organic surfactants which may be so utilized can be anionic, nonionic or ampholytic in nature.

Examples of suitable anionic surfactants are water-soluble salts of the higher alkyl sulfates, such as sodium lauryl sulfate or other suitable alkyl sulfates having 8 to 18 carbon atoms in the alkyl group, water-soluble salts of higher fatty acid monoglyceride monosulfates, such as the sodium salt of the monosulfated monoglyceride of hydrogenated coconut oil fatty acids, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosinate, and the sodium, potassium, and ethanolamine salts of N-lauroyl, N-myristoyl, or N-palmitoyl sarcosinate which should be substantially free from soap or similar higher fatty acid materials.

Other suitable surface-active materials include nonionic agents such as condensates of sorbitan monostearate with ethylene oxide, condensates of ethylene oxide with propylene oxide or, condensates of propylene glycol (available under the trademark "Pluronics"). Other examples of water-soluble nonionic surfactants useful in the dentifrices of the present invention are the condensation products of ethylene oxide with various other compounds which are reactive therewith and have long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, or polyhydric alcohols (e.g., sorbitan monostearate).

The various surfactants may be utilized alone, or in admixture with one another. In toothpastes, the aggregate amount of the surfactant or surfactants used is preferably within the range of about 0.05% to about 5%, more preferably, from about 0.1% to about 1.0%, by weight.

Suitable flavoring and sweetening agents may also be employed in the dentifrices of the invention. Examples of suitable flavorants include the flavoring oils, for example, oils of spearmint, peppermint, wintergreen, sassafras, clove, sage, eucalyptus, marjoram, cinnamon, lemon and orange, as well as methylsalicylate. Suitable sweeteners include sodium cyclamate, perillartine, saccharin, sodium saccharin and ammoniated glycyrrhizin (e.g., its monoammonium salt), and the like. Suitably, the flavoring and sweetening agent together comprise from about 0.01% to 5% or more by weight of the dentifrice. Preferably, the amount of flavoring oil is above 0.3%, e.g. 0.8 to 1.2%.

In a toothpaste, the liquid vehicle comprises water and humectant, typically in an amount ranging from about 10% to about 90% by weight of the preparation. Glycerine, propylene glycol, sorbitol, polypropylene glycol and/or polyethylene glycol (e.g., molecular weight of 400–600) exemplify suitable humectants/carriers. Also advantageous are liquid mixtures of water, glycerine and sorbitol. In translucent gels, where the refractive index is an important consideration, it is preferred to use higher ratios of humectant to water than in opaque pastes.

Toothpastes, creams and gels typically also contain a natural or synthetic thickener or gelling agent in proportions of about 0.1% to about 10%, preferably about 0.5% to about 5%, by weight. Suitable organic thickeners include sodium carboxymethyl cellulose, gum tragacanth, starch, carrageenan, polyvinylpyrrolidone, hydroxyethylpropyl cellulose, hydroxybutyl methyl cellulose, hydroxypropyl methyl cellulose, or hydroxyethyl cellulose, and are usually used in concentrations of 0.1–2.0%. Inorganic thickeners such as hydrated silicas may also be used at levels of about 0.5–10%.

Various other materials may be incorporated in the dentifrices of this invention. Examples thereof are coloring and whitening agents, preservatives, silicones, chlorophyll compounds, and mixtures thereof, and other constituents. These adjuvants are incorporated in the instant compositions in amounts which do not substantially adversely affect the properties and characteristics desired and are selected and used in effective amounts, depending upon the particular adjuvant and type of preparation involved.

The following examples and controls illustrate the invention:

EXAMPLE 1

Example 1 and Control A, shown below, are two phase mineralizing toothpastes delivered from a dual phase pump or split tube. The only significant difference between the two sets of formulations is the ratio of water to humectant in the two phases and the thickener content, carboxymethyl cellulose, in each.

|  | Example 1 | Control A |
|---|---|---|
| Phase A: | | |
| Glycerin | 13.41 | 7.83 |
| CMC 9M8F | 0.25 | 0.40 |
| Water | 5.70 | 11.13 |
| Sodium fluoride | 0.22 | 0.22 |
| Sodium saccharin | 0.50 | 0.50 |
| Sodium carbonate | 0.90 | 0.90 |
| Sodium bicarbonate | 27.00 | 27.00 |
| Anhydrous potassium phosphate dibasic | 0.90 | 0.90 |
| Sodium lauryl sulfate | 0.63 | 0.63 |
| Flavor | 0.50 | 0.50 |
| Phase B: | | |
| Glycerin | 17.28 | 10.91 |
| CMC 9M8F | 0.25 | 0.25 |
| Xanthan gum | 0.15 | 0.30 |
| Methyl paraben | 0.03 | 0.03 |
| Propyl paraben | 0.03 | 0.03 |
| Sorbitol (70% aqueous solution) | 14.50 | 14.50 |
| Water | 5.00 | 10.35 |
| Calcium sulfate | 2.00 | 2.00 |
| Sodium sulfate | 1.50 | 1.50 |
| Sodium saccharin | 0.25 | 0.25 |
| FD&C Blue Dye #1 (1% solution) | 0.15 | 0.15 |
| Thickening silica | 1.00 | 1.00 |
| Abrasive hydtrated silica | 7.00 | 7.00 |
| Sodium lauroyl sulfate | 0.00 | 1.25 |
| Sodium lauryl sulfate | 0.38 | 0.00 |
| Flavor | 0.50 | 0.50 |
| Total | 100.00 | 100.00 |

The water activity of the sodium bicarbonate-phase in Example 1 and Control A was 0.58 and 0.76 respectively. After aging for two weeks in the refrigerator copious amounts of large pyramidal crystals were found in Control A. However, no crystals were found in Example 1 of the invention. Furthermore, crystals developed in Control A even when the product was stored at room temperature. However, no crystals developed in Example 1

EXAMPLE 2

Example 2 and Control B, shown below, represent two tartar control baking soda-based toothpastes utilizing potassium pyrophosphate as the anti-tartar agent.

|  | Example 2 | Control B |
|---|---|---|
| Glycerin | 39.00 | 27.00 |
| CMC 9M8F | 1.00 | 0.7 |
| Water | 16.75 | 29.55 |
| Sodium fluoride | 0.25 | 0.25 |
| Sodium saccharin | 1.00 | 0.50 |
| Sodium bicarbonate | 35.00 | 35.00 |
| Potassium pyrophosphate | 5.00 | 5.00 |
| Sodium lauryl sulfate | 1.00 | 1.00 |
| Flavor | 1.00 | 1.00 |

The water activity of the sodium bicarbonate-toothpaste in Example 2 and Control B was 0.51 and 0.76 respectively. After aging for two weeks in the refrigerator copious amounts of large pyramidal crystals were found in Control B. However, no crystals were found in Example 2 of the invention. Furthermore, crystals developed in Control B even when the product was stored at room temperature. However, no crystals developed in Example 2.

Four toothpaste formulas, including two controls, were made to compare whether the formulations would or would not grow hydrated crystals from the reaction of the sodium bicarbonate and anionic components added to the formulation. In each of Examples 1 and 2, the only changes made to the respective controls A and B are the water content, humectant content, which is glycerin, and thickener content, carboxymethylcellulose.

What is claimed is:

1. A dentifrice or dentifrice phase comprising sodium bicarbonate, an anionic component reactive with sodium and water to form hydrated crystals, said anionic component being selected from the group consisting of orthophosphates, pyrophosphates, polyphosphates, metaphosphates, borates, thiosulfates, and glycerolphosphates, a water content of at least 5 wt. % based on the weight of the dentifrice or dentifrice phase, a humectant in an amount of at least 10 weight % relative to the weight of the dentifrice or dentifrice phase, and optionally at least one of a thickener, or abrasive, said dentifrice or dentifrice phase having a water activity of less than about 0.60.

2. The dentifrice or dentifrice phase of claim 1 wherein said water content is at least 7 wt. % based on the weight of the dentifrice or dentifrice phase.

3. The dentifrice or dentifrice phase of claim 1 wherein said anionic component is a pyrophosphate or polyphosphate anti-tartar agent.

4. The dentifrice or dentifrice phase of claim 1 wherein said anionic component is an orthophosphate, and wherein said dentifrice or dentifrice phase further includes a water-soluble or partially water-soluble calcium salt kept separate from said orthophosphate.

5. The dentifrice or dentifrice phase of claim 1 wherein said sodium bicarbonate is present in amounts of from about 7 to 65% by weight of the dentifrice or dentifrice phase.

6. The dentifrice or dentifrice phase of claim 1 further including a thickener in amounts of from about 0.1 to 10 weight %, based on the weight of the dentifrice or dentifrice phase.

7. The dentifrice or dentifrice phase of claim 1 further including a fluoride salt.

8. The dentifrice or dentifrice phase of claim 6 comprising at least 7 weight % of water.

9. The dentifrice or dentifrice phase of claim 8 further including a fluoride salt.

10. The dentifrice or dentifrice phase of claim 1 further including a surfactant.

11. The dentifrice or dentifrice phase of claim 1 in the form of a toothpaste.

12. The dentifrice or dentifrice phase of claim 1 in the form of a dental cream or gel.

13. The dentifrice or dentifrice phase of claim 3 wherein said pyrophosphate is a mono, di, tri, or tetra-alkali metal pyrophosphate.

14. The dentifrice or dentifrice phase of claim 4 wherein said orthophosphate is selected from alkali metal and ammonium salts of orthophosphoric acid.

15. The dentifrice or dentifrice phase of claim 3 wherein said pyrophosphate is present in amounts of from about 1.5 to 15% by weight of the dentifrice or dentifrice phase.

16. The dentifrice or dentifrice phase of claim 3 wherein said sodium bicarbonate is present in amounts of from about 7 to 65% by weight of the dentifrice or dentifrice phase.

17. The dentifrice or dentifrice phase of claim 4 wherein said sodium bicarbonate is present in amounts of from about 7 to 65% by weight of the dentifrice or dentifrice phase.

18. A dentifrice or dentifrice phase comprising about 7 to 65% by weight sodium bicarbonate, dentifrice or dentifrice phase an anionic component reactive with sodium and water to form hydrated crystals, said anionic component being selected from the group consisting of orthophosphates, pyrophosphates, polyphosphates, metaphosphates, borates, thiosulfates, and glycerolphosphates, a water content of at least 5 wt. % based on the weight of the dentifrice or dentifrice phase, and at least one of a humectant, thickener or abrasive, said dentifrice or dentifrice phase having a water activity of less than about 0.60.

19. The dentifrice or dentifrice phase of claim 18 further including a fluoride salt.

20. The dentifrice or dentifrice phase of claim 18 wherein said anionic component is a pyrophosphate or polyphosphate anti-tartar agent.

21. The dentifrice or dentifrice phase of claim 18 wherein said anionic component is an orthophosphate, and wherein said dentifrice or dentifrice phase further includes a water-soluble or partially water-soluble calcium salt kept separate from said orthophosphate.

22. The dentifrice or dentifrice phase of claim 18 further including a surfactant.

* * * * *